(12) United States Patent
Lee et al.

(10) Patent No.: US 9,808,540 B2
(45) Date of Patent: Nov. 7, 2017

(54) CONTRAST AGENT FOR NUCLEAR MAGNETIC RESONANCE IMAGING COMPRISING MELANIN NANOPARTICLES STABLY DISPERSED IN WATER

(71) Applicants: SNU R&DB FOUNDATION, Seoul (KR); RESEARCH & BUSINESS FOUNDATION SUNGKYUNKWAN UNIVERSITY, Gyeonggi-do (KR)

(72) Inventors: Jin Kyu Lee, Seoul (KR); Kuk Youn Ju, Seoul (KR); Jung Hee Lee, Seoul (KR)

(73) Assignee: Melanis Co., Ltd., Seoul (KR)

( * ) Notice: Subject to any disclaimer, the term of this patent is extended or adjusted under 35 U.S.C. 154(b) by 0 days.

(21) Appl. No.: 14/391,217

(22) PCT Filed: Apr. 9, 2013

(86) PCT No.: PCT/KR2013/002959
§ 371 (c)(1),
(2) Date: Feb. 2, 2015

(87) PCT Pub. No.: WO2013/154329
PCT Pub. Date: Oct. 17, 2013

(65) Prior Publication Data
US 2015/0139914 A1    May 21, 2015

(30) Foreign Application Priority Data

Apr. 9, 2012   (KR) ........................ 10-2012-0037004

(51) Int. Cl.
| | |
|---|---|
| *A61K 49/18* | (2006.01) |
| *A61K 49/10* | (2006.01) |
| *A61K 49/16* | (2006.01) |
| *A61K 49/12* | (2006.01) |

(52) U.S. Cl.
CPC ........ *A61K 49/1818* (2013.01); *A61K 49/103* (2013.01); *A61K 49/106* (2013.01); *A61K 49/126* (2013.01); *A61K 49/16* (2013.01); *A61K 49/186* (2013.01)

(58) Field of Classification Search
None
See application file for complete search history.

(56) References Cited

U.S. PATENT DOCUMENTS

| | | | |
|---|---|---|---|
| 4,855,144 | A | 8/1989 | Leong et al. |
| 5,310,539 | A | 5/1994 | Williams |
| 6,022,526 | A | 2/2000 | Woodburn et al. |
| 8,937,149 | B2 | 1/2015 | Lee et al. |
| 2005/0230347 | A1 | 10/2005 | Gallas et al. |
| 2007/0237829 | A1* | 10/2007 | Dadachova ......... A61K 9/0019 424/489 |
| 2008/0057001 | A1 | 3/2008 | Sun |
| 2011/0200534 | A1 | 8/2011 | Cheon et al. |
| 2012/0205590 | A1 | 8/2012 | Lee et al. |

FOREIGN PATENT DOCUMENTS

| | | |
|---|---|---|
| CN | 101233196 A | 7/2008 |
| EP | 0 313 380 | 4/1989 |
| EP | 0 639 209 B1 | 1/1998 |
| EP | 1 911 812 A1 | 4/2008 |
| JP | 08-500371 A | 1/1996 |
| JP | 2007-023150 A | 2/2007 |
| KR | 10-0051256 | 5/1992 |
| KR | 10-2010-0023778 | 3/2010 |
| KR | 10-2011-0044712 | 4/2011 |
| KR | 10-2012-0003631 | 1/2012 |
| KR | 10-1227322 | 1/2013 |
| KR | 10-1729710 | 4/2017 |
| KR | 10-1729711 | 4/2017 |
| WO | WO 01/18125 A1 | 3/2001 |
| WO | WO 2007/010861 A1 | 1/2007 |
| WO | WO 2011/049406 | 4/2011 |
| WO | WO 2013/154329 A1 | 10/2013 |

OTHER PUBLICATIONS

Schweitzer et al. Melanin-covered nanoparticles for protection of bone marrow during radiation therapy of cancer. 2010 Int. J. Radiat. Oncol. Biol. Phys. 78: 1494-1502.*
Gu et al. Nuclear penetration of surface functionalized gold nanoparticles. 2009 Toxicol. Appl. Pharmacol. 237: 196-204.*
Dijkers et al. Biodistribution of 89Zr-trastuzumab and PET imaging of HER2-positive lesions in patients with metastatic breast cancer. 2010 Clin. Pharmacol. Ther. 87: 586-592.*
International Search Report for PCT/KR2013/002959, mailed Jul. 3, 2013.
Korytowski, W. et al., "Oxygen Activation During the Interaction Between MPTP Metabolites and Synthetic Neuromelanin—An ESR-Spin Trapping, Optical, and Oxidase Electrode Study," Biochemical and Biophysical Research Communications 154:781-788 (1988), Academic Press, Inc.
Meredith, P. et al., "Towards Structure-Property-Function Relationships for Eumelanin," Soft Matter, 2:37-44 (2005), The Royal Society of Chemistry, London, UK.
Peter, M.G., "On the Structure of Eumelanins: Identification of Constitutional Patterns by Solid-State NMR Spectroscopy", Angew Chem. Int. Ed., Engl. 28 (1989) VCH Velagsgesellschaft mbH, Weinheim, Germany.
Nagaraja, P. et al., "Spectrophotometric Methods for the Determination of Certain Catecholamine Derivatives in Pharmaceutical Preparations," Talanta 46 pp. 39-44 (1998), Elsevier Science B.V., Amsterdam, Netherlands.

(Continued)

*Primary Examiner* — Michael G Hartley
*Assistant Examiner* — Jennifer Lamberski
(74) *Attorney, Agent, or Firm* — Rubin and Rudman LLP

(57) ABSTRACT

The present invention relates to a contrast agent for nuclear magnetic resonance imaging, and more particularly, to a contrast agent for nuclear magnetic resonance imaging containing melanin nanoparticles having a uniform shape and size, thereby providing good dispersibility in water, no cell toxicity, and a long retention time in vivo.

33 Claims, 11 Drawing Sheets

(56) References Cited

OTHER PUBLICATIONS

English translation of Chinese Office Action of Appl. No. CN201080047906 dated Mar. 6, 2013, issued by the State Intellectual Property Office of People's Republic of China.
Extended European Search Report of EP Appl. No. 10825231.3 dated Jan. 7, 2014, issued by European Patent Office.
English translation of International Search Report of PCT/KR2010/007288 dated Jul. 28, 2011, issued by Korean Intellectual Property Office.

* cited by examiner

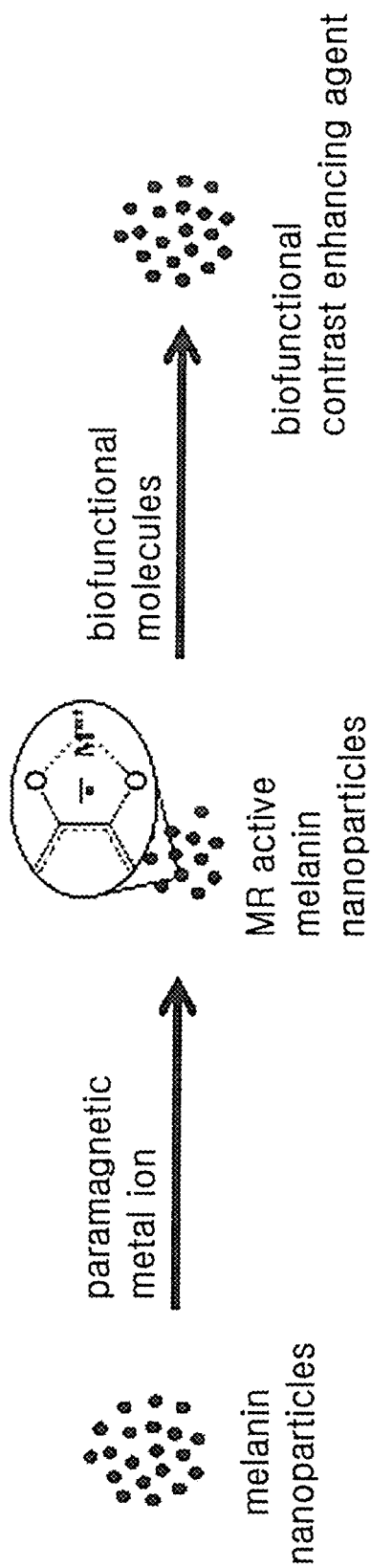
[Fig. 1]

[Fig. 2]
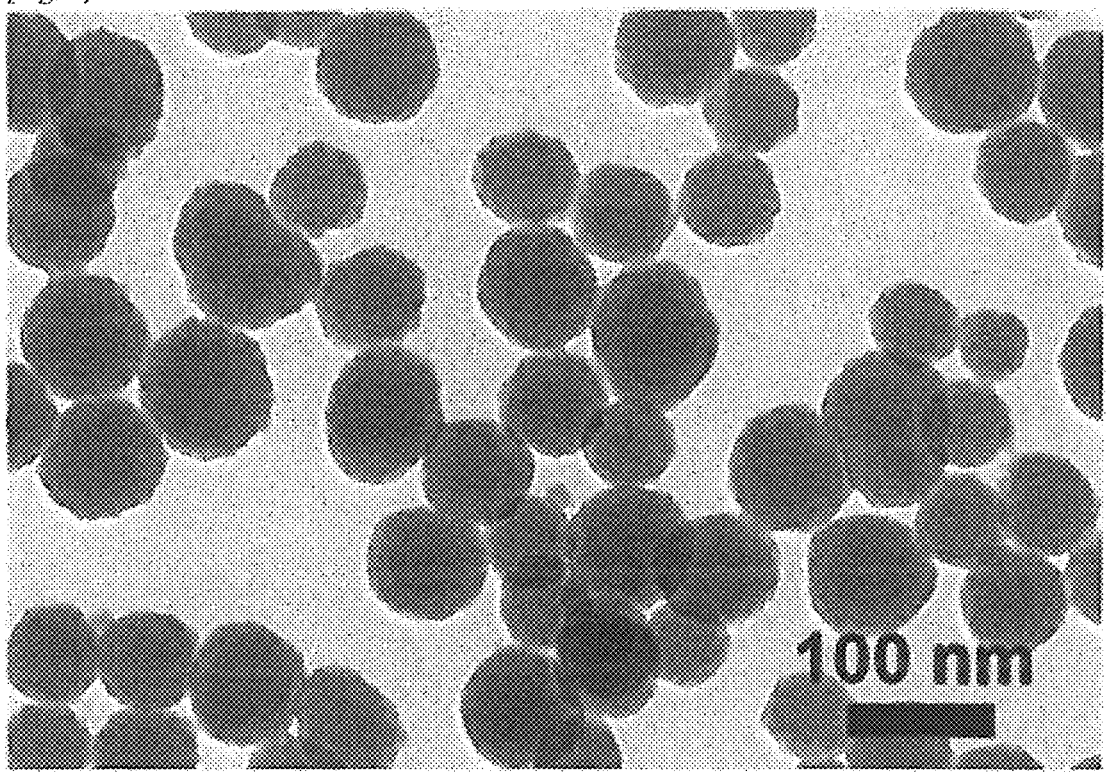
[Fig. 3]
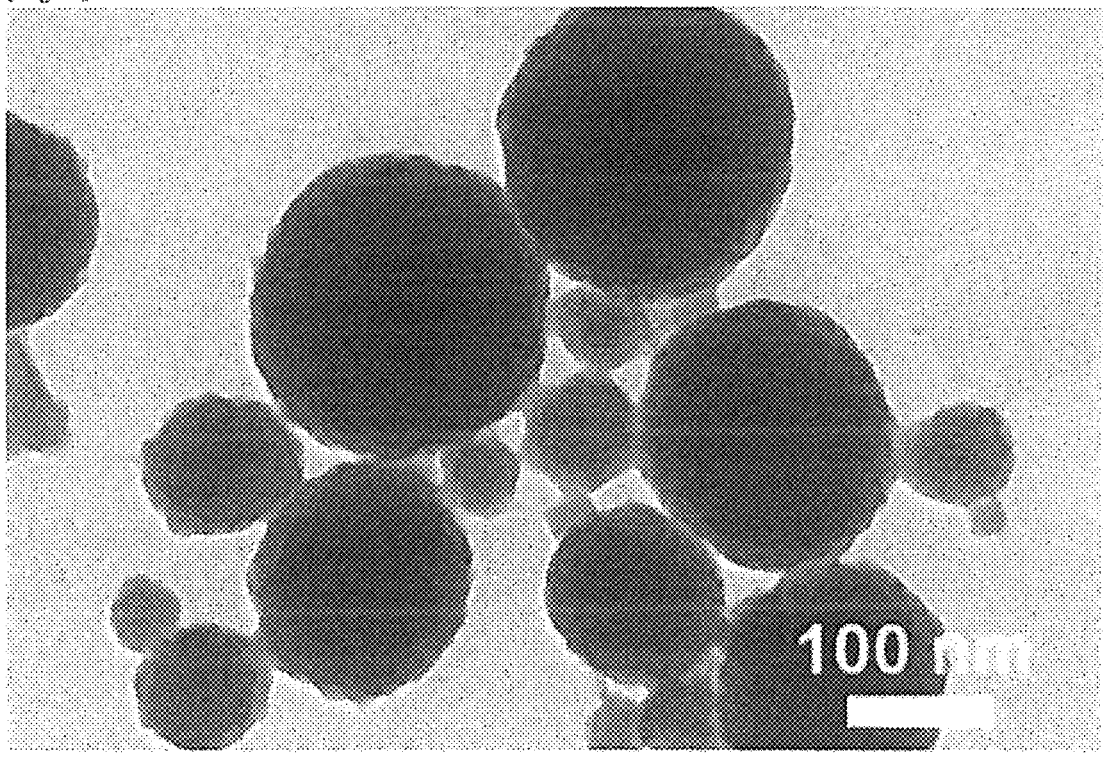

[Fig. 4]
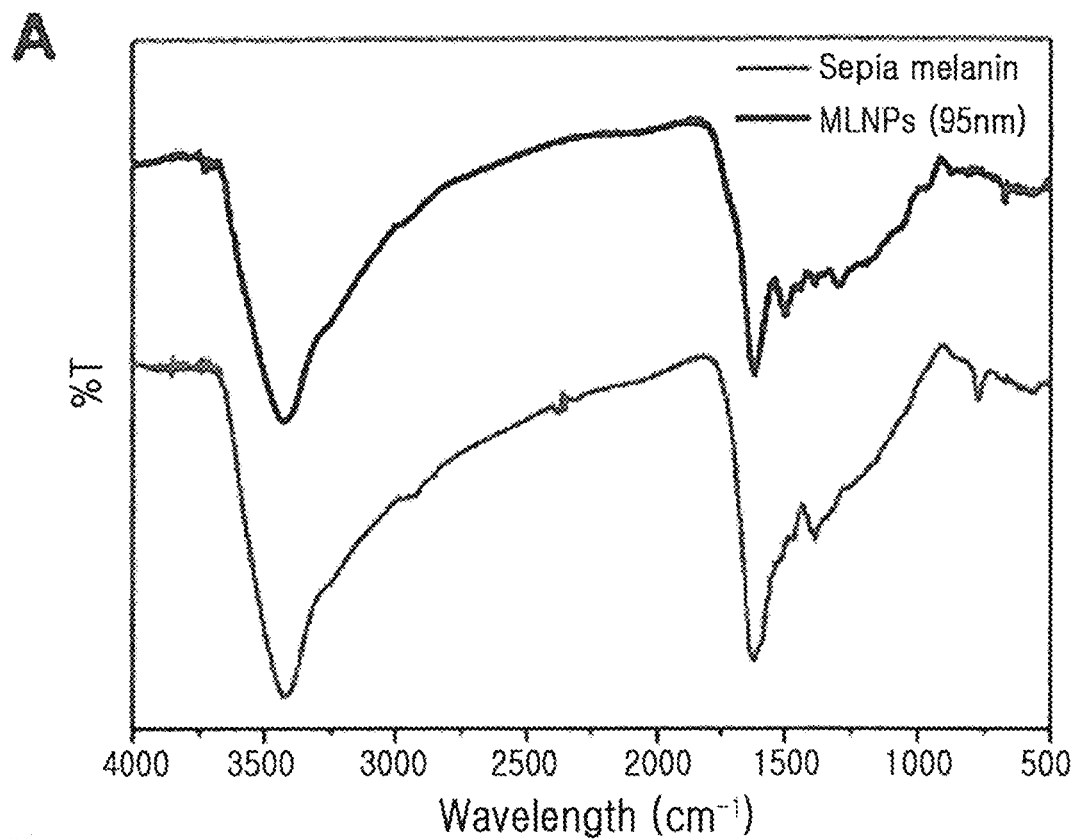
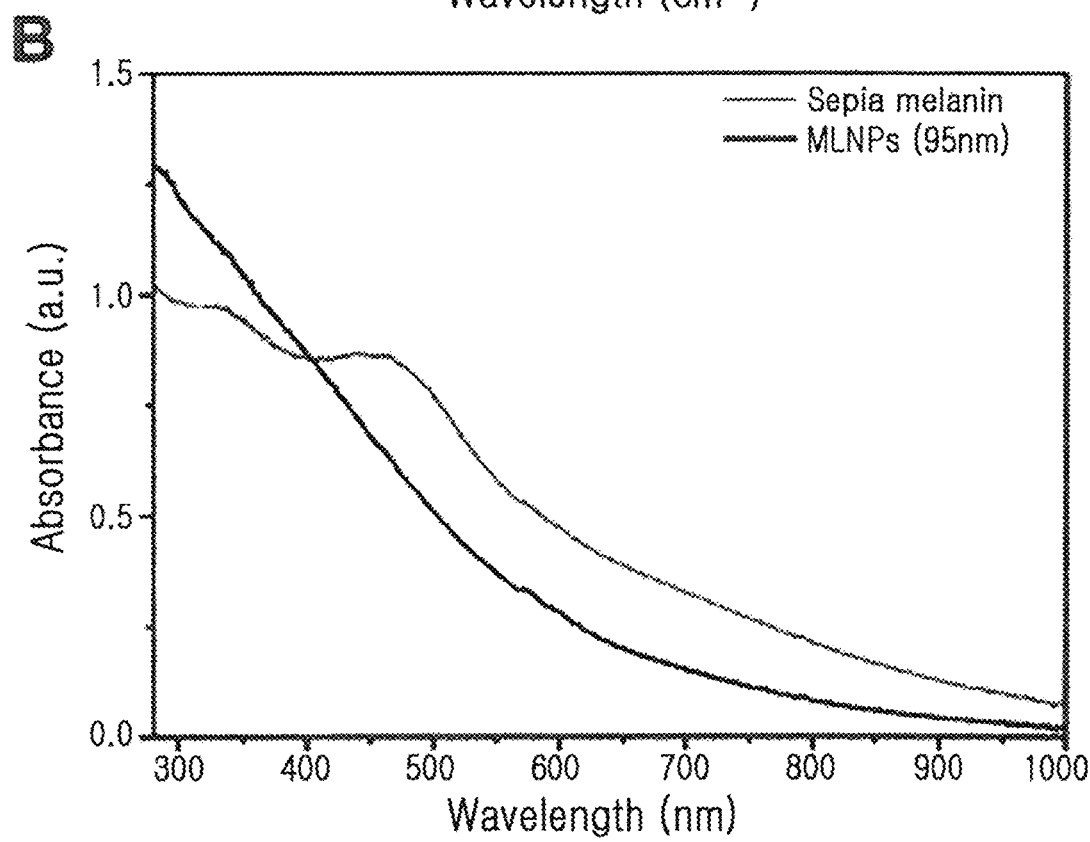

[Fig. 5]
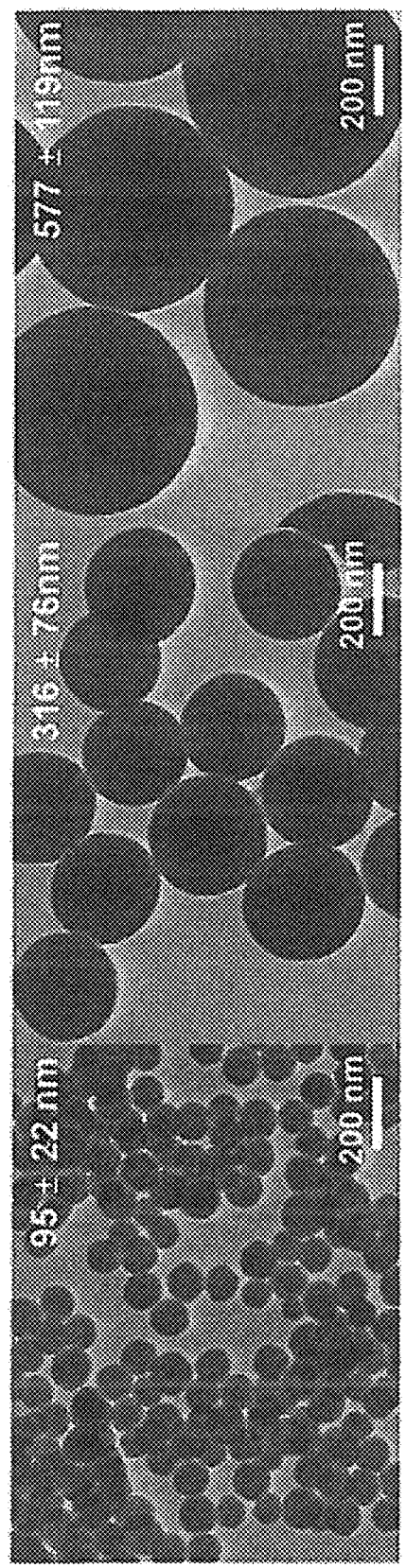

[Fig. 6]
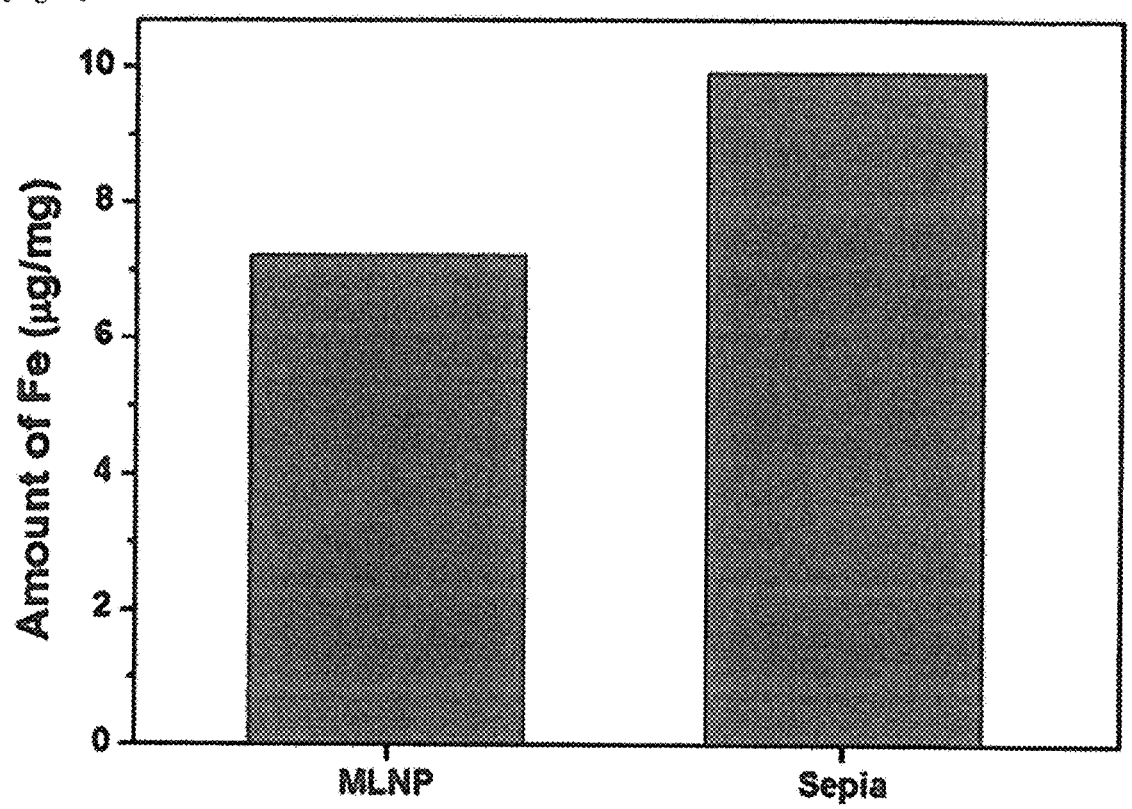

[Fig. 7]
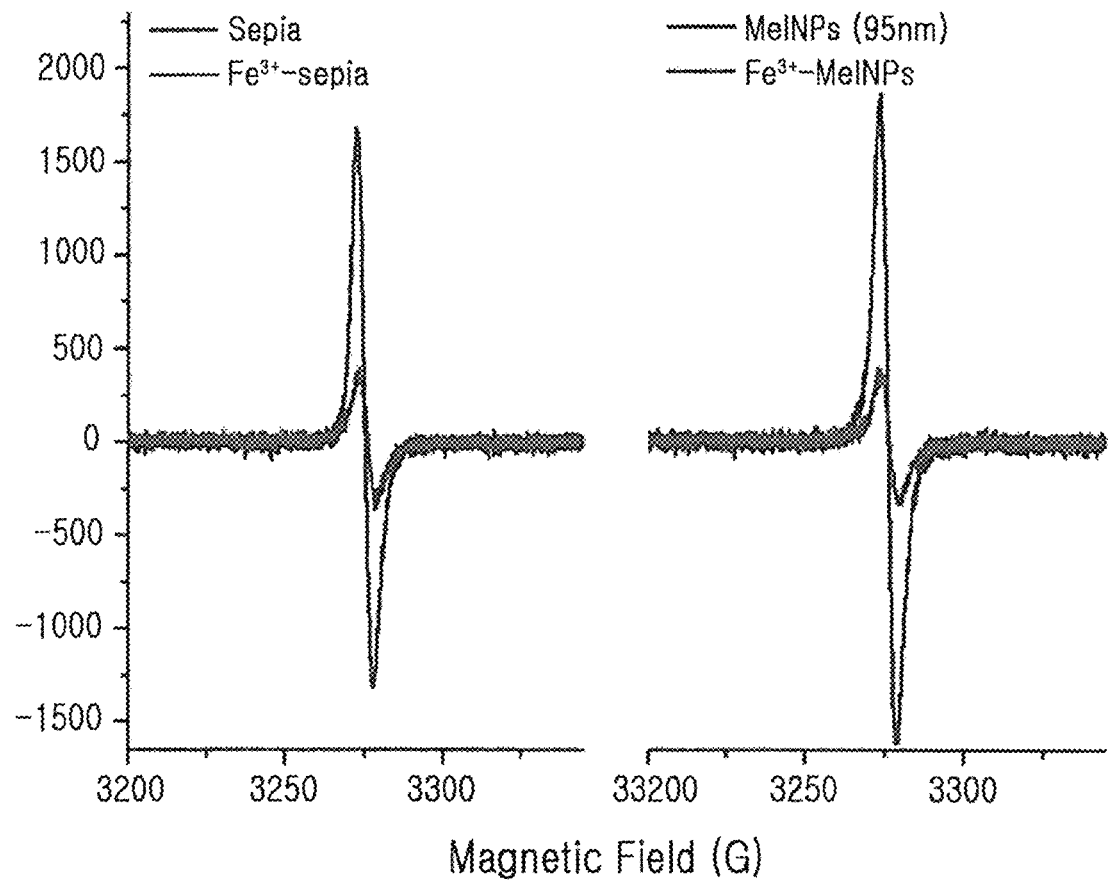
[Fig. 8]
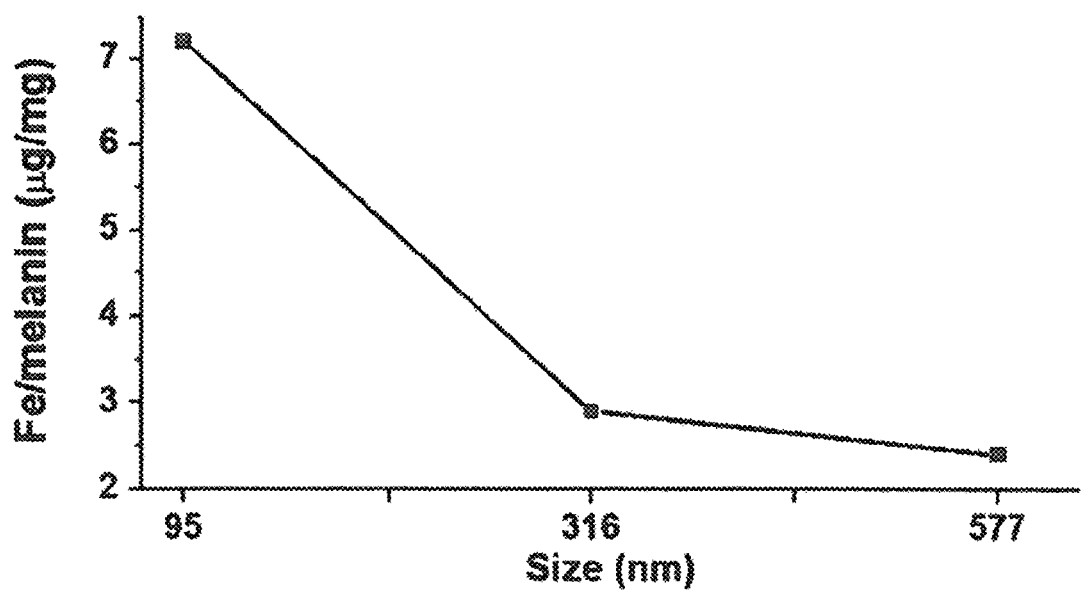

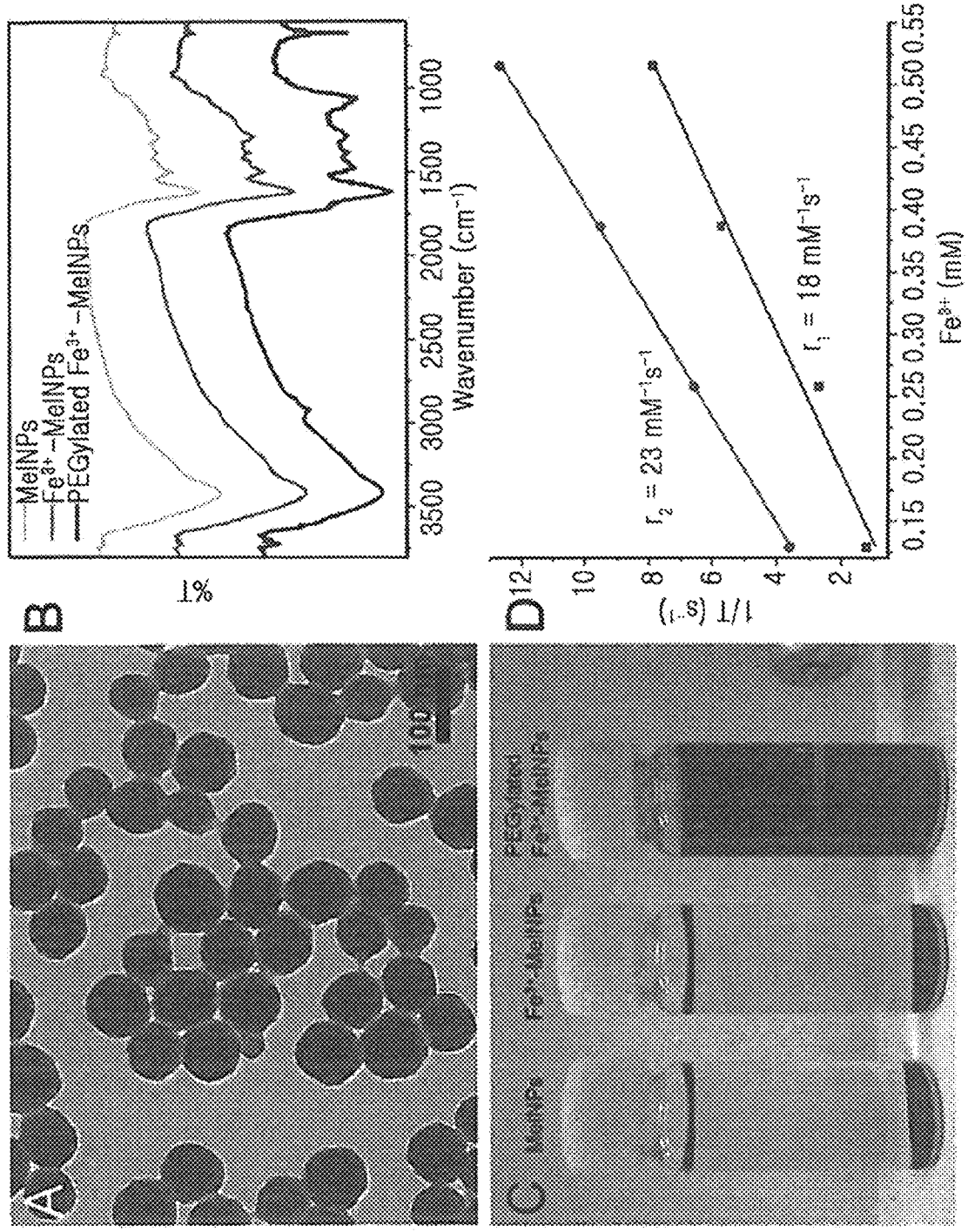
[Fig. 9]

[Fig. 10]
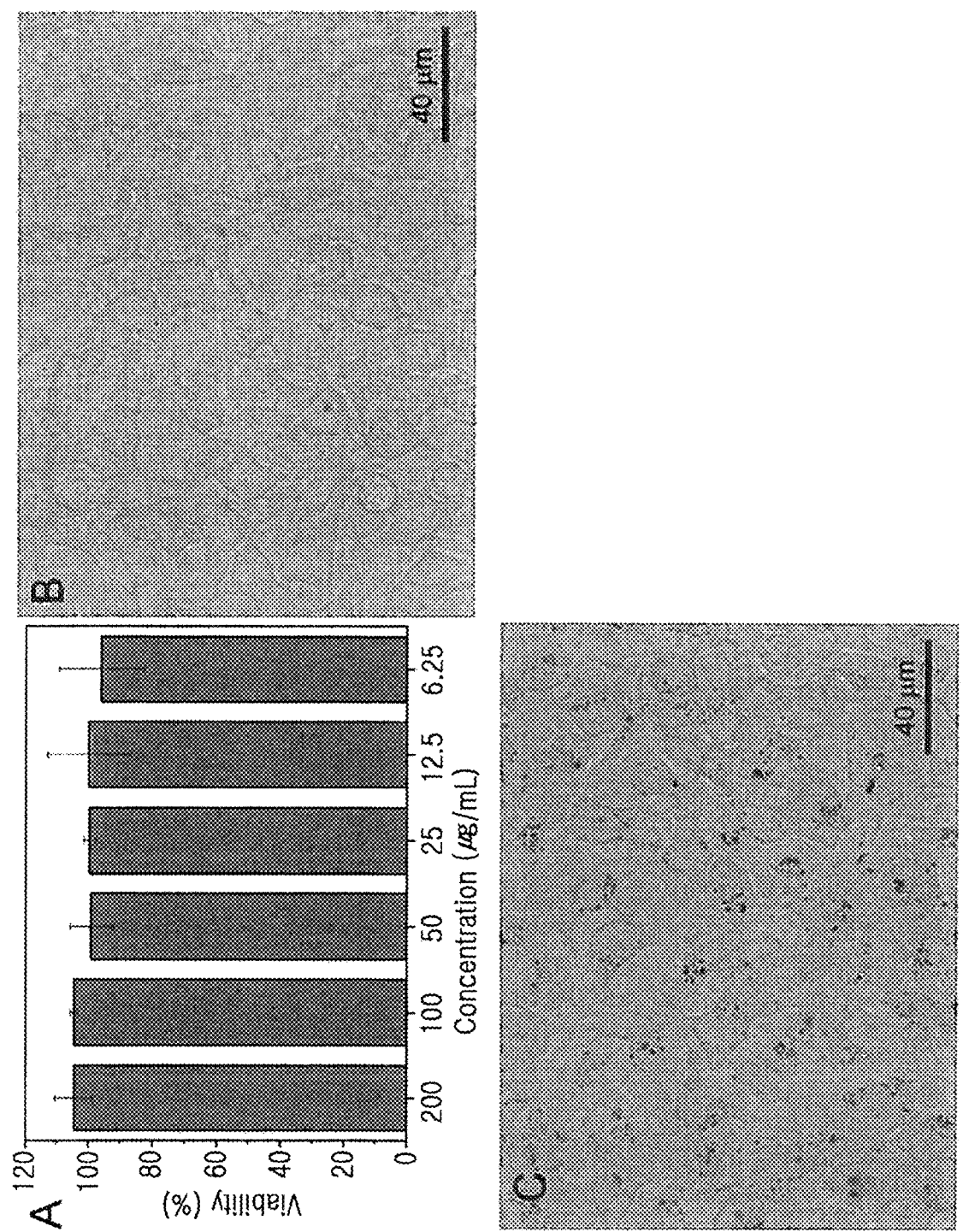

[Fig. 11]
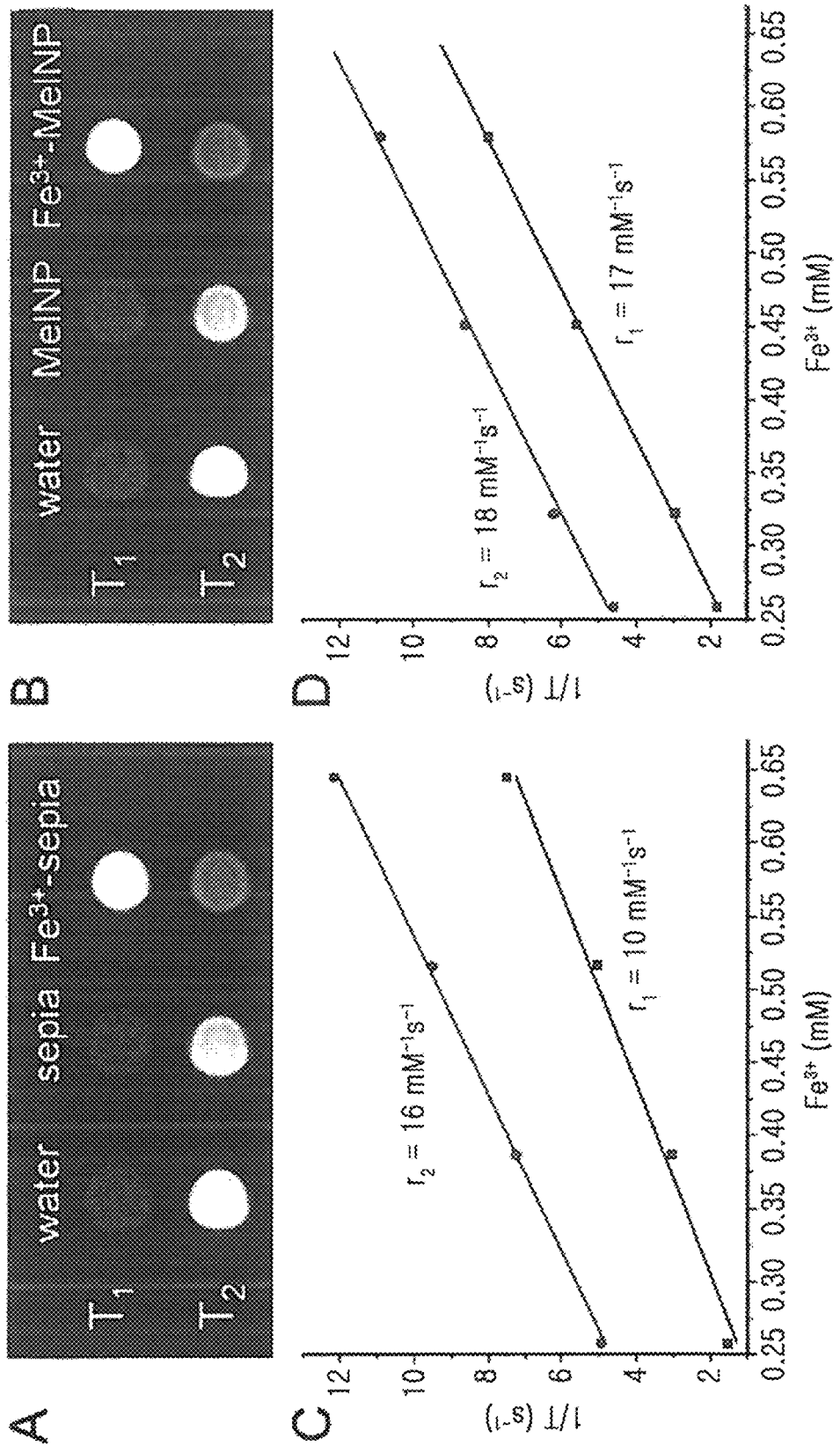

CONTRAST AGENT FOR NUCLEAR MAGNETIC RESONANCE IMAGING COMPRISING MELANIN NANOPARTICLES STABLY DISPERSED IN WATER

TECHNICAL FIELD

The present invention relates to a contrast agent for nuclear magnetic resonance imaging, which has good dispersibility in water, no cytotoxicity, and a long retention time in vivo, thereby being usefully applied as an MRI contrast agent.

BACKGROUND ART

Magnetic resonance imaging (MRI) is a rapidly developing diagnostic imaging modality, which detects magnetic resonance signals emitted from water molecules after irradiation of low electromagnetic energy into a sample. Magnetic resonance imaging allows repeatable acquisitions of non-invasive magnetic resonance images to study tissue anatomy with high resolution for a short time, and therefore, it is known as the most suitable method for diagnosing a patient's disease and monitoring drug treatment. Signal intensity of magnetic resonance imaging is determined by two time parameters, which are T1 and T2 relaxation time and by proton density of water molecule from spin density. With regard to the contrast of magnetic resonance imaging, magnetic resonance images of a sample are controlled by a contrast agent.

Gadolinium (Gd) agents are representative of the paramagnetic T1 contrast agent. However, the gadolinium (Gd) agent itself is highly toxic, and therefore, its safety must be improved it the form of chelates. For instance, a MRI contrast agent (Gd-DTAP) prepared by chelating Gd with diethylenetriamine pentaacetic acid (DTAP) is frequently used.

However, most T1 contrast agents including Gd-DTPA are not specific to organs, tissues, or particular cells, but most of them are contrast agents for imaging blood vessels of the tissues. Further, the conventional contrast agents nave a short retention time in vivo, and therefore, efforts to improve the retention time have been made.

Meanwhile, melanins are biopolymers that are widely distributed in many parts of living organisms such as plants, animals, and protista, and are usually categorized into black-brown eumelanins and yellow-reddish pheomelanins. Eumelanins are derived from 3,4-dihydrozy-L-phenyl alanine (L-DOPA) or 2-(3,4-dihydroxyphenyl)ethylamine (dopamine), and pheomelanins are derived from L-DOPA or dopamine in the presence of mercapto group (—SH)-containing compounds such as cysteine, glutathione, etc. Eumelanins are predominantly found in mammals, and are known to be biopolymers having irregular polymeric structures, including the indole units which are formed from catecholamines by intramolecular addition of the amino groups to the oxidatively generated o-quinones.

Melanoma in the body is Known to show strong T1-MRI signals through, a coordinate bond with paramagnetic metal ions in the body, suggesting detection of melanoma in the body by MRI and possibility of MRI probes by using melanin.

However, it is difficult to obtain pure melanins, because many biological materials such as proteins other than melanins are also obtained when obtained from natural sources. In addition, even though the biological materials are removed by purification, melanin particles themselves are damaged to reduce their contrasting effect. Meanwhile, melanins which are obtained by the conventional synthetic method are not dispersed in water, and thus there was a limitation in their use as a biological contrast agent. In particular, it is difficult to use the melanins in vivo because of the low dispersibility in water. In addition, although it injected into the body, they are precipitated/aggregated, or rapidly excreted from the body. Thus, there is a disadvantage that a desired contrasting effect cannot be obtained.

Accordingly, the present inventors prepared melanin nanoparticles having a predetermined size and shape, and formed coordinate bonds between the melanin nanoparticles and paramagnetic ions, and modified the surface of the melanin nanoparticles with PEGs. They found that these melanin nanoparticles have good dispersibility in water, no cytotoxicity, and a long retention time in vivo, so as to be usefully applied as an MRI contrast agent, thereby completing the present invention.

DISCLOSURE

Technical Problem

An objective of the present invention is to provide a contrast agent for nuclear magnetic resonance imaging, which has good dispersibility in water, no cytotoxicity, and a long retention time in vivo, thereby being usefully applied as an MRI contrast agent.

Another objective of the present invention is to provide a method for preparing the contrast agent for nuclear magnetic resonance imaging.

Technical Solution

In order to achieve the above objectives, the present invention provides a contrast agent for nuclear magnetic resonance imaging, including melanin nanoparticles having stable dispersibility in water; paramagnetic metal ions which are coordinated to melanin of the melanin nanoparticles; and PEGs which are attached to the surface of the melanin nanoparticles for surface modification.

As used herein, the term 'nuclear magnetic resonance image' means imaging based on the nuclear magnetic resonance phenomenon which occurs due to absorption of the energy during the transition to another energy level by action of a particular external energy on a magnetic moment of atomic nucleus in a magnetic field.

The present invention is to provide a contrast agent for nuclear magnetic resonance imaging, which is characterized in that melanin nanoparticles are used as basic particles of the contrast agent and paramagnetic metal ions showing strong nuclear magnetic resonance signals are bound to melanins of the melanin nanoparticles via coordinate bonds.

As used herein, the term 'melanin' means a biological polymer that is distributed in many parts of living organisms such as plaints, animals, and protista, and is usually categorized into black-brown eumelanins and yellow-reddish pheomelanins. In the present invention, melanin nanoparticles are used, and the diameter of the melanin nanoparticle is 30 nm to 600 nm and preferably 30 nm to 200 nm. The melanin nanoparticles are stably dispersed in neutral water for 30 days or longer. After surface treatment with PEGs, they are stably dispersed in waiter for 180 days or longer.

The melanin nanoparticles can be obtained from natural sources or by chemical synthetic methods. When obtained from natural sources, they can be recovered, from the ink of cuttlefish by centrifugation. When synthesized by chemical methods, they can be synthesized from a melanin precursor of dopamine, DOPA or cysteine. For example, a method including the following steps can be used for preparation:

1) Step of neutralization by adding a base to a solution containing dopamine.$H^+X^-$, and 2) Step of polymerization of dopamine of the solution of step 1)

wherein a molar ratio of dopamine.$H^+C^-$ and the base is 1:0.1 to 1:1.

Step 1 is a step of neutralization by reacting dopamine.$H^+X^-$ with a base, in which melanin can be prepared into nanoparticles having a. predetermined, shape by controlling a molar ratio of dopamine.$H^+X^-$ and, the base at 1:0.1 to 1:1. Step 2 is a step of preparing melanin nanoparticles by polymerization after neutralization with the base.

The $X^-$ may be selected from the group consisting of halide ions, $HSO_4^-$, $NO_3^-$, $H_2PO_4^-$ and $CH_3COO^-$. Further, the base may be selected from the group consisting of alkali metal hydroxides, alkaline earth metal hydroxides, alkali metal carbonates, alkaline earth metal carbonates, alkali metal bicarbonates, alkaline earth metal bicarbonates, alkali metal acetates, alkali metal phosphates, alkali metal alkozides (1-20 carbon atoms), ammonia ($NH_3$), ammonium hydroxide ($NH_4OH$), and amine.

The melanin nanoparticles prepared by the above preparation method are characterized in that they nave a more uniform particle shape and better dispersibility in water than melanin nanoparticles obtained from natural sources.

Further, the contrast agent for nuclear magnetic resonance imaging of the present invention is characterized in that the paramagnetic metal ions form coordinate bonds with melanins of melanin nanoparticles.

As used herein, the term 'paramagnetic metal ion' means a material showing nuclear magnetic resonance image, in which internal unpaired spins are randomly oriented due to thermal motion, but in a magnetic field, the spins can align to a predetermined direction. That is, it means a material that retains no magnetism as usual, but it is magnetized toward the magnetic field when an external magnetic field is applied. Examples thereof may include ions of one or more metals selected from the group consisting of gadolinium (Gd), iron (Fe), manganese (Mn), nickel (Ni), copper (Cu), erbium (Er), europium (Eu), holmium (Ho) and chromium (Cr).

The paramagnetic metal ion may form a coordinate bond with melanin of the melanin nanoparticle, which is shown in FIG. 1. When the paramagnetic metal ion is coordinated to melanin of the melanin nanoparticle, it shows a stronger T1 shortening effect than the conventional Gd-based contrast agents, thereby exhibiting an excellent contrast effect of nuclear magnetic resonance imaging in T1-weighted images.

The paramagnetic metal ion can be bound in an amount of 1 μg to 10 μg, and preferably 2 μg to 7 μg, based on the weight of melanin nanoparticles. further, as the size of melanin nanoparticle decreases, the surface area of the melanin nanoparticle relative to its weight increases. Therefore, the melanin nanoparticle having a small size is preferred, in the light of the binding amount of the paramagnetic metal ion.

Further, the contrast agent for nuclear magnetic resonance imaging of the present invention is characterized in that the surface of the melanin nanoparticle is modified with amine- or thiol-functionalized PEGs (polyethylene glycol). The 'PEG (polyethylene glycol)' used in the present invention is used for dispersing melanin nanoparticles in water, and the molecular weight of PEG is preferably 1 KDa to 40 KDa.

Dispersibility of melanin nanoparticles in water is greatly increased by PEG modification. According to one embodiment of the present invention, melanin nanoparticles without PEG modification are precipitated in water, but melanin nanoparticles modified with PEGs are well dispersed in water and thus can maintain the suspension state. When the particles have improved dispersibility in water, they exist in the body for a long time, and therefore, it is possible to secure the time taken for attaching the melanin nanoparticles to particular tissues or cells, thereby effectively obtaining the desired contrast effect.

According to one embodiment of the present invention, even at 24 hours after injection of the contrast agent for nuclear magnetic resonance imaging according to the present invention, the contrast effect can be obtained, indicating that this contrast agent is more excellent than the conventional contrast agent for nuclear magnetic resonance imaging which shows the contrast effect for a short time.

Further, the contrast agent for nuclear magnetic resonance imaging of the present invention is characterized in that the surface of the melanin nanoparticles is further modified with 3-mercaptopropionic acid, together with PEGs.

Further, the contrast agent for nuclear magnetic resonance imaging of the present invention is characterized in that the surface of the melanin nanoparticle is further bound with an antibody. Because various functional groups exist on the surface of the melanin nanoparticles of the present invention, antibodies can be bound thereto. The antibody is to provide a function of improving the contrast effect by bending the melanin nanoparticles to a desired region, for example, a specific tissue or cell. The antibody that can be used in the present invention may be Cetuximab or Herceptin, but is not limited thereto.

According to one embodiment of the present invention, the antibody-bound contrast agent for nuclear magnetic resonance imaging of the prevention can be accumulated in specific cells, thereby improving the contrast effect.

Further, the present invention provides a method for preparing the contrast agent for nuclear magnetic resonance imaging, including the following steps of:

adding a solution containing the paramagnetic metal ions to a solution containing the melanin nanoparticles to form coordinate bonds between the paramagnetic metal ion and melanin of the melanin nanoparticles (Step 1);

adding PEGs to the solution of Step 1) (Step 2); and recovering the prepared melanin nanoparticles from the solution, of Step 2) (Step 3).

The melanin nanoparticles, paramagnetic metal ion, and. PEGs are the same as described above.

Step 1 is a step of forming coordinate bonds between the paramagnetic metal ion and melanin of the melanin nanoparticles. The solution containing the paramagnetic metal ions is added to the solution containing melanin nanoparticles, and then stirred for approximately 3 hours to form coordinate bonds.

Step 2 is a step of modifying the surface of the melanin nanoparticles with PEGs. In this regard, the solution containing PEGs may be added to the solution of Step 1. Alternatively, the melanin nanoparticles prepared in Step 1 are recovered by centrifugation, dried and washed, and then dispersed in water, and to this dispersed solution, the solution containing PEGs may be added.

Further, 3-mercaptopropionic acid is further added to Step 2, thereby modifying the surface of melanin nanoparticles with PEGs and 3-mercaptopropionic acid.

Further, the method may further include the step of binding the prepared, melanin nanoparticles with antibodies.

The contrast agent for nuclear magnetic resonance imaging according to the present invention has no cytotoxicity, and a long retention time in vivo, compared to the conventional contrast agent for nuclear magnetic resonance imaging, thereby being usefully applied as an MRI contrast agent. According to one embodiment of the present invention, the contrast agent for nuclear magnetic resonance imaging according to the present invention showed excellent $r_2/r_1$, compared to $Fe_2O_3$, MnO, Hollow $Mn_3O_4$, and showed $r_2/r_1$ similar to that of Gd-DTPA. Further, Gd-BTPA shows a snort contrast effect whereas the contrast agent for nuclear magnetic resonance imaging according to the present invention has a long retention time in vivo and therefore, it is more effective to secure the time taken for attachment to particular tissues or cells.

Further, various functional groups exist on melanins of the melanin nanoparticles, and thus they con be used for binding antibodies to the surface of the melanin nanoparticles. According to one embodiment of the present invention, antibodies specific to particular cells (cancer cells) are bound thereto, thereby effectively obtaining MRI images for particular cells.

Advantageous Effects

The contrast agent for nuclear magnetic resonance imaging according to the present invention contains melanin nanoparticles having a uniform. shape and size, thereby providing good dispersibility in water, no cytotoxicity, and a long retention time in vivo. Thus the contrast agent for nuclear magnetic resonance imaging according to the present invention is usefully applied as an MRI contrast agent.

DESCRIPTION OF DRAWINGS

FIG. 1 is a schematic illustration showing formation of coordinate bonds between paramagnetic metal ions and melanins of melanin nanoparticles;

FIG. 2 is a TEM image of melanin nanoparticles (MelNPs) according to one embodiment of the present invention;

FIG. 3 is a TEM image of melanin nanoparticles (sepia melanin) according to one embodiment of the present invention;

FIG. 4 shows IR spectra (FIG. 4A) and UV/Vis spectra (FIG. 4B) of melanin nanoparticles (MelNPs and sepia melanin) according to one embodiment of the present invention;

FIG. 5 is a TEM image of melanin nanoparticles (MelNPs) according to one embodiment of the present invention;

FIG. 6 shows the result of measuring $Fe^{3+}$ concentrations of $Fe^{3+}$-coordinated melanin nanoparticles ($Fe^{3+}$-MelNPs and $Fe^{3+}$-sepia melanin) according to one embodiment of the present invention;

FIG. 7 shows ESR signals of $Fe^{3+}$-coordinated melanin nanoparticles ($Fe^{3+}$-MelNPs and $Fe^{3+}$-sepia melanin) according to one embodiment of the present invention;

FIG. 8 shows the result of measuring size-dependent $Fe^{3+}$ concentrations of $Fe^{3+}$-coordinated melanin nanoparticles ($Fe^{3+}$-MelNPs and $Fe^{3+}$-sepia melanin) according to one embodiment of the present invention;

FIG. 9 shows a TEM image (FIG. 9A) FT-IR spectra (FIG. 9B), dispersibility (FIG. 9C), and T1 excitation time graph (FIG. 9D) of PEGylated $Fe^{3+}$-coordinated melanin nanoparticles (PEGylated $Fe^{3+}$-MelNPs) according to one embodiment of the present invention;

FIG. 10 shows viability of HeLa cells by treatment of PEGylated $Fe^{3+}$-coordinated melanin nanoparticles (PEGylated $Fe^{3+}$-MelNPs) according to one embodiment of the present invention, in which FIG. 10A shows cell viability according to concentrations of melanin nanoparticles, FIG. 10B snows a non-treated control group, and FIG. 10C shows the result of PEGylated $Fe^{3+}$-MelNPs treatment;

FIG. 11 shows MRI properties of $Fe^{3+}$- coordinated melanin nanoparticles ($Fe^{3+}$-MelNPs and $Fe^{3+}$-sepia melanin) according to one embodiment of the present invention, in which each concentration of the melanin nanoparticles was 4 mg/mL; (a) $T_1$ and $T_2$ weighted MR images obtained from Sepia before and after chelation with $Fe^{3+}$ion (b) $T_1$ and $T_2$ weighted MR images of MelNP before and after chelation with $Fe^{3+}$ion (c) plot of $1/T_1$ and $1/T_2$ against Fe concentration of $Fe^{3+}$-Sepia and (d) $Fe^{3+}$-MelNP FIG. 13 shows T1-weighted MRI image of PEGylated $Fe^{3+}$-coordinated melanin nanoparticles (PEGylated $Fe^{3+}$-MelNPs) according to one embodiment of the present invention, in which FIG. 13A shows the result of PEGylated $Fe^{3+}$-MelNPs, FIG. 13B shows the result of IgE-bound PEGylated $Fe^{3+}$-MelNPs, and FIG. 13C shows the result of Cetuximab-bound PEGylated $Fe^{3+}$-MelNPs.

MODE FOR DISCLOSURE

Figure 12:
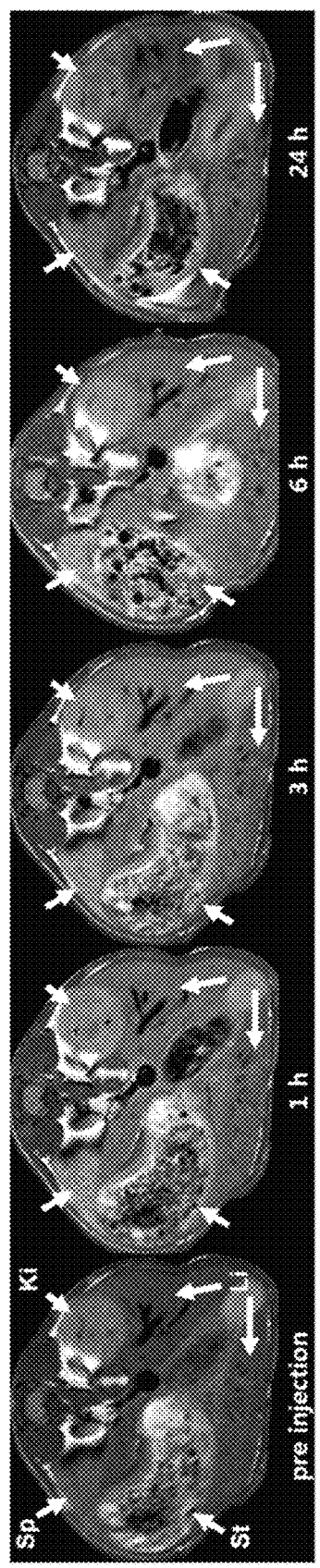
FIG. 12 shows T1-weighted MRI image of PEGylated $Fe^{3+}$-coordinated melanin nanoparticles (PEGylated $Fe^{3+}$-MelNPs) according to one embodiment of the present invention, in which Sp indicates spleen, Ki indicates kidney, Li indicates liver, and St indicates stomach.

Hereinafter, the present invention will be described in more detail with reference to Examples. however, these Examples are for illustrative purposes only, and the invention is not intended to be limited by these Examples.

EXAMPLE 1

Preparation of Melanin Nanoparticles

1) Example 1-1 (MelNPs)

180 mg of dopamine hydrochloride (Aldrich Chemical) was dissolved in 90 mL of deionized water. 760 μl of 1 N NaOH solution was added to the dopamine hydrochloride solution at 50° C. with vigorous stirring. When NaOH was added, the solution immediately changed to light yellow, and gradually to deep brown. After reaction for 5 hours, melanin nanoparticles were recovered by centrifugation (18,000 rpm), and washed with deionized water several times. Precipitates were removed after low speed centrifugation (4000 rpm), and then melanin nanoparticles were stored as a dispersibility solution.

2) Example 1-2 (MelNPs)

Melanin nanoparticles were prepared in the same manner as in Example 1-1, except that the addition amount, of NaOH was from 400 to 950 μ, the amount of deionized water was from 45 to 180 mL, and the reaction temperature was from 20 to 70° C.

In detail, 180 mg of dopamine hydrochloride was dissolved in 90 mL of tri-distilled water, and then 760 μl of 1 N NaOH was added thereto with vigorous stirring at room temperature. After 5 hours, melanin nanoparticles having a size of 316 nm were obtained by several centrifugations. Further, melanin nanoparticles having a size of 577 nm were obtained in the same manner, except that the amount of 1 N NaOH was reduced to 450 μl.

3) Example 1-3 (Sepia Melanin)

Ink sacs were obtained from dissection of Korean cuttlefish, and sepia melanin was extracted therefrom by syringe.

Sepia melanin was centrifuged (18,000 rpm) and washed five times, and then re-dispersed in water and stored.

TEM images of the melanin nanoparticles prepared in Examples 1-1 and 1-3 were obtained on Hitachi-7600 electron microscope, and the results are shown in FIG. 2 (Example 1-1) and FIG. 3 (Example 1-3).

As shown in FIG. 2, the melanin nanoparticles prepared in Example 1-1 had an average diameter of approximately 95 nm, and the shape and size of the prepared nanoparticles were uniform. In contrast, as shown in FIG. 3, the sepia melanin prepared in Example 1-3 had a diameter of 30 to 200 nm, and the size of the particles was irregular.

Further, the infrared spectra of the melanin nanoparticles prepared in Examples 1-1 and 1-3 were obtained with a JASCO FT-IR-600 Plus, and UV/vis spectra were obtained on a SINCO S-3100. The results are shown in FIG. 4. As shown in FIG. 4, the infrared spectra and Uv/vis spectra of the melanin nanoparticles prepared in Examples 1-1 and 1-3 were similar to each other.

Further, TEM images of the melanin nanoparticles prepared in Example 1-2 were also obtained on Hitachi-7600 electron microscope, and the results are shown in FIG. 5.

EXAMPLE 2

Preparation of Paramagnetic Metal Ion-coordinated Melanin Nanoparticles

1) Example 2-1 ($Fe^{3+}$-MelNPs)

100 μl of $Fe^{3+}$ solution (1 mg/mL) was added to 10 ml of melanin nanoparticles solution (1 mg/mL) prepared in Example 1-1 with vigorous stirring. After 3 hours, $Fe^{3+}$-coordinated melanin nanoparticles were recovered by centrifugation (19,000 rpm), and the supernatant was fettered using a membrane filter (0.45 μm pore size) and $Fe^{3+}$ concentration was measured by ICP-AES to calculate the amount of $Fe^{3+}$ bound to the melanin nanoparticles.

The $Fe^{3+}$-coordinated melanin nanoparticles thus recovered were washed with deionized water several times, and diluted and stored.

2) Example 2-2 ($Fe^{3+}$-MelNPs)

$Fe^{3+}$-coordinated melanin nanoparticles were prepared in the same manner as in Example 2-1, except that the melanin nanoparticles prepared in Example 1-2 were used instead of the melanin, nanoparticles prepared in Example 1-1.

2) Example 2-3 ($Fe^{3+}$-sepia Melanin)

$Fe^{3+}$-coordinated melanin nanoparticles were prepared in the same manner as in Example 2-1, except that the melanin nanoparticles prepared in Example 1-3 were used instead of the melanin nanoparticles prepared in Example 1-1.

The concentrations of $Fe^{3+}$ coordinated, in Examples 2-1 and 2-3 were measured and the results are shown in FIG. 6.

Further, the ESR spectra of $Fe^{3+}$-coordinated melanin nanoparticles prepared in Examples 2-1 and 2-3 and non-$Fe^{3+}$-coordinated melanin nanoparticles prepared in Examples 1-1 and 1-3 were recorded on a JEOL JES-FA200, and the results are shown in FIG. 7. As shown in FIG. 7, ESR signal intensities of Examples 2-1 and 2-3 were reduced compared, to Examples 1-1 and 1-3, respectively. The reduction in ESR signal intensities indicates formation of coordinate bonds between the paramagnetic metal ions, $Fe^{3+}$ ions and the dihydroxyl groups of melanin nanoparticles.

Further, the concentration of the coordinated $Fe^{3+}$ of the $Fe^{3+}$ coordinated melanin nanoparticles prepared, in Example 2-2 was measured and the results are shown in FIG. 8. As shown in FIG. 8, as the size of melanin nanoparticles increases, the amount of the coordinated $Fe^{3+}$ decreases.

EXAMPLE 3

Preparation of PEGylated Paramagnetic Metal Ion-coordinated Melanin Nanoparticles (PEGylated $Fe^{3+}$-MelNPs)

150 mg of methoxy-poly(ethylene glycol)thiol (mPEG-SH; 2 kDa; SunBio (Korea)) was added, to 10 mL of $Fe^{3+}$-coordinated melanin nanoparticles solution (1 mg/mL) prepared in Example 2-1, and $NH_4OH$ solution (28 wt %) was added to adjust the pH of the solution to approximately 10.3. After stirring for 1 hour. surface-modified melanin nanoparticles were recovered by centrifugation (18,000 rpm), and washed with deionized water several times using redispersibility/centrifugation processes so as to prepare PEGylated $Fe^{3+}$-coordinated melanin nanoparticles.

The TEM images and FT-IR spectra of the prepared melanin nanoparticles were measured and shown in FIGS. 9A and 9B, respectively. Further, the dispersibility of the prepared melanin nanoparticles was observed with the naked eye (FIG. 9C), and plots of T1 excitation time vs $Fe^{3+}$ concentration were obtained (FIG. 9D).

EXAMPLE 4

Preparation of MPA/PEG-bound Paramagnetic Metal Ion-coordinated Melanin Nanoparticles 160 mg of methozy-poly(ethylene glycol)thiol (mPEG-SH; 2 kDa; SunBio (Korea)) and 10 mL of MPA (3-mercaptopropionic acid) were added to 10 mL of $Fe^{3+}$-coordinated melanin nanoparticles solution (1 mg/mL) prepared in Example 2-1, and $NH_4OH$ solution (28 wt %) was added to adjust the pH of the solution to approximately 10.3. After stirring for 1 hour, surface-modified melanin nanoparticles were recovered by centrifugation (18,000 rpm), and washed with deionized water several times using redispersibility/centrifugation processes so as to prepare PEG bound $Fe^{3+}$-coordinated melanin nanoparticles.

EXAMPLE 5

Preparation of Antibody-bound Melanin Nanoparticles

Example 5-1) Preparation of Cetuximab-bound Melanin Nanoparticles 0.2 μmol of EDC hydrochloride (1-ethyl-3-(3-dimethylaminopropyl)-carbodiimide(EDC) hydrochloric) was added to 1 mL of melanin nanoparticles solution (1 mg/mL) prepared in Example 4. After stirring for 1 hour, 4 μl of Cetuximab solution (1 mg/mL) was added and stirred for 4 hours and recovered Cetuximab-bound melanin nanoparticles by a purification process of centrifugation/redispersibility.

EXAMPLE 5-2

Preparation of IgG-bound Melanin Nanoparticles

IgE-bound melanin nanoparticles were prepared in the same manner as in Example 5-1, except that IgG antibody was used instead of Cetuximab.

EXPERIMENTAL EXAMPLE 1

Cytotoxicity Assay

Cell viability was tested by the WST-1 assay. Cells (HeLa cell) were cultured on 96-well plates at a density of $3/10^3$ cells/well for 24 hours, followed by treatment with mPEG-SH-surface treated melanin nanoparticles (PEGylated $Fe^{3+}$-MelNPs) prepared in Example 3. After 24 hours of culture with increasing concentrations, 10 μl of WST-1 solution (2-(4-nitrophenyl)-5-(2-sulfophenyl)-3-[4-(4-sulfophenylazo)-2-sulfophenyl]-2H-tetrazolium disodium salt, Daeli Science, Korea) was added to each well, and the plates were cultured for an additional 1 hour at 37° C. The absorbance of each well at 455 nm was measured with a reference at 630 nm by using a Bio-Tek model ELx800™ microplate reader (Bio-Tek Instruments, Winooski, Vt.), and the absorbance from the melanin nanoparticles themselves was compensated. The percentage of cell viability was calculated using the following formula:

% cell viability=(mean absorbance in test wells)/(mean absorbance in control well)×100.

Each experiment was performed in triplicate, and the results are shown in FIG. 10. As shown in FIG. 10, when HeLa cells were treated with 200 g/mL, their viability was 100%, indicating that mPEG-SH-surface treated melanin nanoparticles (PEGylated $Fe^{3+}$-MelNPs) did not show any cytotoxicity, and thus they leave high biocompatibility.

EXPERIMENTAL EXAMPLE 3

MRI Relaxation Properties

The $Fe^{3+}$-coordinated melanin nanoparticles (Examples 2-1 ($Fe^{3+}$-MelNPs) and 2-3 ($Fe^{3+}$-sepia melanin)) were prepared in Eppendorf tubes at varying concentrations. Their T1 and T2 relaxation times were measured on a 3.0 T clinical MRI scanner (Philips, Achieve ver. 1.2, Philips Medical Systems, Best, The Netherlands, 80 mT/m gradient amplitude, 200 ms/m slew rate). A Loot-Locker sequence (TR/TE=10/1 ms; flip angle=5°) was used to acquire 17 gradient echo images at different inversion delay times (minimum inversion time: 87 ms, phase interval: 264 ms, in-plane image resolution: 625×625 mm², slice thickness: 500 mm). The images were fitted into 3-parameter function to calculate T1 values by using a Matlab program. T2 measurements were performed using 10 different times in a multislice turbo spin echo sequence (TR/TE=5000/20, 40, 60, 80, 100, 120, 140, 160, 180, 200 ms, in-plane resolution; 200×200 mm², slice thickness: 500 mm). The images were processed using the Levenberg-Marquardt method to calculate T2 values using a Matlab program. $r_1$ and $r_2$ were calculated from the plots of T1-1 and T2-1 versus concentration of the contrast agent. The signal intensities for each of the ROIs on the T1 map (60-80 pixels) and the T2 map (200-300 pixels) were measured for each concentration, which were then used for $r_1$ and $r_2$ calculations, respectively. Relaxivities were derived based on the molar concentration of iron atoms measured using ICP-AES. The results are shown in FIG. 11.

Further, Gd-DTPA, $Fe_2O_3$, MnO, and Hollow $Mn_3O_4$ were measured as control groups in the same manner. The results are shown in the following Table 1.

TABLE 1

| Contrast agent | Diameter (nm) | $r_1$ $(mM^{-1} S^{-1})$ | $r_2$ $(mM^{-1} S^{-1})$ | $r_2/r_1$ | $B_0$ (T) |
|---|---|---|---|---|---|
| Gd-DTPA | molecule | 4.5 | 5 | 1.1 | 3 |
| $Fe_2O_3$ | 2.2 | 4.7 | 17.5 | 3.6 | 3 |
| MnO | 7 | 0.3 | 1.7 | 4.7 | 3 |
| Hollow $Mn_3O_4$ | 20 | 1.4 | 7.7 | 5.5 | 3 |
| Example 2-1 | 95 | 17 | 18 | 1.1 | 3 |
| Example 2-3 | 30-200 | 10 | 16 | 1.6 | 3 |

EXPERIMENTAL EXAMPLE 4

In vivo MRI Experiment

In vivo MRI was carried on a 7T/20 micro-MRI System (Bruker-Biospin, Fallanden, Switzerland) equipped with a 20 cm gradient set capable of supplying up to 400 mT/m in a 100 μs rise time. A birdcage coil (72 mm i.d.; Bruker-Biospin, Fallanden, Switzerland) was used for excitation, and an actively decoupled phased array coil was used to receive the signal.

During MRI, the animals were anesthetized with inhalation of 2% isoflurane. The rectal temperature was carefully monitored and maintained at 36±1° C. The melanin nanoparticles prepared in Examples 3, 5-1 and 5-2 were intravenously administered through a tail vein of a mouse in an amount of 20 mg per 1 kg of body weight, of the mouse. The amount of Fe injected was 144 μg per 1 kg of body weight of the mouse, when measured, by ICP-AES. To investigate the time course distributions of the injected melanin nanoparticles in the mouse body, MRI was performed before and 1, 3, 6, 24, 48 hrs after the administrations.

High-resolution melanin nanoparticle contrast-enhanced MR images were obtained from each mouse abdomen by using a FSE (fast spin-echo) $T_1$-weighted MRI sequence and a FSE (fast spin-echo) $T_2$-weighted MRI sequence. All images were analyzed using Paravasion software (Bruker-Biospin, Fallanden, Switzerland). The sequence parameters are the same as follows.

FSE (fast spin-echo) $T_1$-weighted MRI sequence

Repetition time (TR)/echo time (TE)=300/7.9 ms, number of experiment (NEX)=4, echo train length=2, 100×100 μm² in plane resolution, a slice thickness: 800 μm, 10 slices)

FSE (fast spin-echo) $T_2$-weighted MRI sequence

Repetition time (TR)/echo time (TE)=3000/60 ms, number of experiment (NEX)=4, echo train length=4, 100/100 μm² in plane resolution, a slice thickness: 800 μm, 10 slices)

The results are shown in FIG. 12. After injection of PEGylated $Fe^{3+}$-MelNPs, T1-weighted MRI images in the spleen and the liver were observed within 1 hour, respectively, because of the selective accumulation of PEGylated $Fe^{3+}$-MelNPs in the cells of RES (reticuloendotherial system).

After 6 hrs, the liver seemed to return to a similar contrast to that before administration, out apparently high T1-weighted MRI images in the spleen persisted. After 24 hours, all organs seemed to return to normal contrast, indicating the degradation and/or clearance of PEGylated $Fe^{3+}$-MelNPs, and also indicating that melanins snow biocompatibility similar to other biomaterials, unlike other inorganic nanoparticles.

Figure 13:
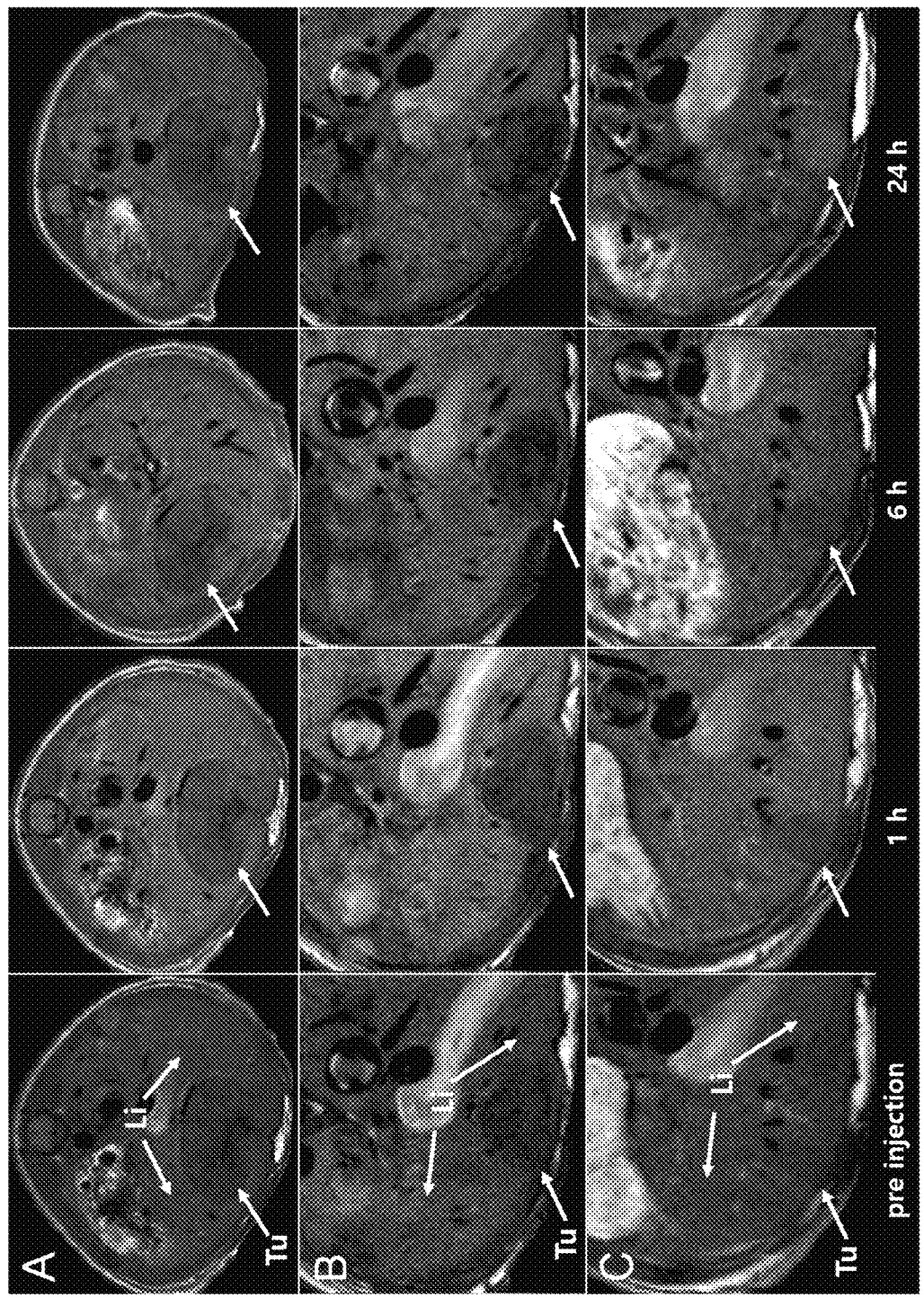

Experiments were performed in the same manner as above, except that liver cancer-transplanted mice were used, and the results are shown in FIG. 13A.

1 hour after injection of PEGylated $Fe^{3+}$-MelNPs, $T_1$-weighted MPI images were obtained from the normal liver tissue, but not from the cancer tissue (FIG. 13A). Such selective accumulation in the normal liver is attributed to pseudonegative contrast of tumor, which can be also explained by the difference in the activity or amount of RES cells between cancer cells and normal liver cells.

Experiments were also performed in the same manner as above, except that liver cancer-transplanted mice were used, and antibody-bound PEGylated $Fe^{3+}$-MelNPs were used, and the results are shown in FIGS. 13B and 13C.

Up to 6 hours after injection of Cetuximab-bound PEGylated $Fe^{3+}$-MelNPs for selective targeting liver cancer, the same images as in the normal liver were observed. After 24 hours, the normal liver returned, to the contrast similar to that before injection but the tumor was clearly visualized (FIG. 13C).

These tissue-specific targeting results can be compared with the results (FIG. 13B) of pseudonegative contrast of tumor by IgG-bound PEGylated $Fe^3$ +-MelNPs.

The invention claimed is:

1. A contrast agent for nuclear magnetic resonance imaging, comprising:
    melanin nanoparticles having stable dispersibility in water; and
    paramagnetic metal ions which are coordinated on the surface of the melanin nanoparticles.

2. The contrast agent according to claim 1, wherein the melanin is obtained from the ink of cuttlefish and has a diameter of 30 nm to 600 nm.

3. The contrast agent according to claim 1, wherein the melanin nanoparticle is synthesized from a melanin precursor of dopamine, DOPA or cysteine, and has a diameter of 30 nm to 600 nm.

4. The contrast agent according to claim 1, wherein the paramagnetic metal ion is one or more metal ions selected from the group consisting of gadolinium (Gd), iron (Fe), manganese (Mn), nickel (Ni), copper (Cu), erbium (Er), europium (Eu), holmium (Ho) and chromium (Cr).

5. The contrast agent according to claim 1, wherein the surface of the melanin nanoparticles is modified with 3-mercaptopropionic acid.

6. The contrast agent according to claim 1, wherein an antibody is bound to the surface of the melanin nanoparticles.

7. The contrast agent according to claim 6, wherein the antibody is Cetuximab or Trastuzumab.

8. The contrast agent of claim 1, further comprising polyethyleneglycol (PEG) attached to the surface of the melanin nanoparticles for surface modification.

9. The contrast agent according to claim 8, wherein the surface of the melanin nanoparticles is modified with amine- or thiol- functionalized PEG.

10. The contrast agent according to claim 8, wherein the PEG has a molecular weight of 1 KDa to 40 KDa.

11. The contrast agent according to claim 8, wherein the surface of the melanin nanoparticles is modified with 3-mercaptopropionic acid.

12. The contrast agent according to claim 8, wherein an antibody is bound to the surface of the melanin nanoparticles.

13. A method for preparing a contrast agent for nuclear magnetic resonance imaging comprising melanin nanoparticles having stable dispersibility in water and paramagnetic metal ions which are coordinated on the surface of the melanin nanoparticles, the method comprising:
    adding a solution containing paramagnetic metal ions to a solution containing melanin nanoparticles to form coordinate bonds between the paramagnetic metal ions and melanin of the melanin nanoparticles, and forming melanin nanoparticles having stable dispersibility in water.

14. The method according to claim 13, further comprising adding 3-mercaptopropionic acid.

15. The method according to claim 14, further comprising binding the prepared melanin nanoparticles with an antibody.

16. The method according to claim 15, wherein the antibody is Cetuximab or Trastuzumab.

17. The method according to claim 13, wherein the melanin is obtained from the ink of cuttlefish and has a diameter of 30 nm to 600 nm.

18. The method according to claim 13, wherein the melanin nanoparticles are synthesized from a melanin precursor of dopamine, DOPA or cysteine, and have a diameter of 30 nm to 600 nm.

19. The method according to claim 13, wherein the paramagnetic metal ion is one or more metal ions selected from the group consisting of gadolinium (Gd), iron(Fe), manganese (Mn), nickel (Ni), copper (Cu), erbium (Er), europium (Eu), holmium (Ho) and chromium (Cr).

20. The method of claim 13, further comprising adding polyethyleneglycol (PEG) to the solution containing paramagnetic metal ions and melanin nanoparticles.

21. The method according to claim 20, wherein the PEG has a molecular weight of 1 KDa to 40 KDa.

22. The method according to claim 20, wherein the melanin nanoparticles are synthesized from a melanin precursor of dopamine, DOPA or cysteine, and have a diameter of 30 nm to 600 nm.

23. The method according to claim 20, wherein the paramagnetic metal ion is one or more metal ions selected from the group consisting of gadolinium (Gd), iron(Fe), manganese (Mn), nickel (Ni), copper (Cu), erbium (Er), europium (Eu), holmium (Ho) and chromium (Cr).

24. A contrast agent produced by the method of claim 13.

25. A contrast agent produced by the method of claim 20.

26. The contrast agent according to claim 25, wherein the melanin is obtained from the ink of cuttlefish and has a diameter of 30 nm to 600 nm.

27. The contrast agent according to claim 25, wherein the melanin nanoparticles are synthesized from a melanin precursor of dopamine, DOPA or cysteine, and have a diameter of 30 nm to 600 nm.

28. The contrast agent according to claim 25, wherein the paramagnetic metal ion is one or more metal ions selected from the group consisting of gadolinium (Gd), iron (Fe), manganese (Mn), nickel (Ni), copper (Cu), erbium (Er), europium (Eu), holmium (Ho) and chromium (Cr).

29. The contrast agent according to claim 25, wherein the surface of the melanin nanoparticles is modified with amine- or thiol-functionalized PEG.

30. The contrast agent according to claim 25, wherein the PEG has a molecular weight of 1 KDa to 40 KDa.

31. The contrast agent according to claim 25, wherein the surface of the melanin nanoparticles is modified with 3-mercaptopropionic acid.

32. The contrast agent according to claim 25, wherein an antibody is bound to the surface of the melanin nanoparticles.

33. The contrast agent according to claim 32, wherein the antibody is Cetuximab or Trastuzumab.

* * * * *